United States Patent [19]

Stark

[11] Patent Number: 4,578,757

[45] Date of Patent: Mar. 25, 1986

[54] METHOD FOR PREVENTING COLLISION OF TWO MUTUALLY MOVABLE BODIES AND AN APPARATUS INCLUDING AN ARRANGEMENT FOR PREVENTING COLLISION

[75] Inventor: Johan S. H. Stark, Stockholm, Sweden

[73] Assignee: U.S. Philips Corporation, New York, N.Y.

[21] Appl. No.: 469,364

[22] Filed: Feb. 24, 1983

[30] Foreign Application Priority Data

Feb. 24, 1982 [SE] Sweden .................................. 8201149

[51] Int. Cl.[4] .............................................. B25J 9/00
[52] U.S. Cl. ...................................... 364/461; 364/513; 250/363 R
[58] Field of Search ............... 364/461, 513, 559, 439, 364/463; 340/685, 686; 250/363.5 SC, 363.8 SF; 343/455

[56] References Cited

U.S. PATENT DOCUMENTS

| | | | |
|---|---|---|---|
| 3,920,972 | 11/1975 | Corwin, Jr. et al. ................. | 364/513 |
| 4,017,721 | 4/1977 | Michaud .............................. | 364/513 |
| 4,028,533 | 6/1977 | Matsubara ........................... | 364/513 |
| 4,063,073 | 12/1977 | Strayer ................................ | 364/439 |
| 4,402,350 | 9/1983 | Ehret et al. ......................... | 364/463 |

Primary Examiner—Errol A. Krass
Assistant Examiner—Thomas G. Black
Attorney, Agent, or Firm—Jack E. Haken; James J. Cannon, Jr.

[57] ABSTRACT

The invention relates to a method and a device for prevention of collision between two mutually and independently movable bodies (A, B). In the method the outer contour of each body is approximated by a number of virtual subvolumes, preferably spheres ($SA_1$, $SA_2$), whereafter the position of the centrum point ($c_1$, $c_2$) of each such sphere, when the respective body assumes a zero or reference position, is stored in a fixed memory together with the radius ($r_1$, $r_2$) of each sphere. Repeatedly during a motion the new position of each sphere ($SA_1$, $SA_2$) is determined by means of the stored positions and the output signals from position transducers associated to the bodies (A, B) and finally the distance between each sphere of one body (A) and each sphere of the second body (B) is calculated. These calculated distances indicate the risk for collision and must exceed a given threshold value. In an anti-collision system said calculated distances may be used to generate signals, which automatically brake or stop the motion of the bodies.

5 Claims, 6 Drawing Figures

METHOD FOR PREVENTING COLLISION OF TWO MUTUALLY MOVABLE BODIES AND AN APPARATUS INCLUDING AN ARRANGEMENT FOR PREVENTING COLLISION

BACKGROUND OF THE INVENTION

1. Field of the Invention

The invention relates to a method to determine the risk of collision for two mutually movable bodies, which cooperate with transducers for continuous monitoring of the positions of the bodies during a motion. Suitably in case of risk for collision a signal can be delivered, which automatically brakes or stops the motion of the bodies so that collision is prevented. Furthermore it relates to a device for carrying out the method.

The invention can be used in many circumstances, where two or more bodies can move arbitrarily and independently of each other. As an example equipment can be mentioned where several apparatus parts shall be set relative to a patient table, which is also movable in itself, hoisting cranes, overhead cranes, industrial robots and the like, which can move relative to fixed construction or other movable bodies. In such cases, where two or more bodies are included, which can move in several directions, it is often difficult to predict all situations when collision may occur. An operator, who controls and supervises the motion of the bodies, can often not see simultaneously all movable parts and with the new combinations of mutual positions of the bodies, which can arise collision then may occur in a part of the equipment, while the operator has his attention directed to another part of the equipment.

2. Description of the Prior Art

It has previously been proposed to solve the problem by prescribing conditions for the motion of the bodies, so that only certain motions are allowed, while other motions under given conditions are forbidden. Thus, it is possible in each position of a body to calculate forbidden positions or motion zones of another body. The result of these calculations can then be put into a table or be stored in another manner. For each adjustment then the operator first must look up in the table if a certain setting motion is allowed or not. This is complicated and in spite thereof does not given fully satisfactory results, because the tabled information is only a coarse information and cannot cover all possible mutual positions of the bodies.

SUMMARY OF THE INVENTION

The object of the invention is to propose a method and an apparatus provided with an arrangement for preventing collision and thereby preventing collision without need of any restrictions on the motions of the bodies.

According to the invention this is achieved by repeatedly determining during the motion, the position for the centrum of a number of virtual subvolumes which together approximate the outer contour of the respective body, and that the distance between those subvolumes which represent one of the bodies and those subvolumes which represents the other body is determined by means of the obtained centrum positions and the known size of the subvolumes, whereafter this distance is compared with a safety distance. The subvolumes are preferably spheres which has the advantage that the distance between them will be the same independently of their mutual orientation.

By the fact that the outer contour of each body in this manner is represented by a restricted number of subvolumes, which preferably are shaped as spheres, the position of which in space is fully defined by the coordinates for their centrum points, the information quantity which must be stored and processed in order to get an opinion about the outer contour of the bodies in each moment will also be limited, because it is sufficient to store the coordinates of the said centrum points together with the radii of the spheres and, in case of a motion, to determine the new coordinates of the centrum points. The risk of collision is then determined by calculating the distance between those spheres which represent one of the bodies and those spheres which represent the other body and to compare this distance with a safety distance.

In principle the distance from each sphere on one of the bodies to each sphere on the other body must be calculated and the total number of distance calculations therefore will be equal to the product of the number of spheres representing the first body and the number of spheres representing the second body. In order to reduce the number of distance calculations the number of the spheres shall be as small as possible but in order to have a good approximation of the outer contour the number shall be large. The choice of the number of spheres will be a compromise between these two desires.

In order to reduce the total calculation work the spheres may be approximated in a first calculation step with cubes thereby that the distance between the projections of the spheres on the axes in an orthogonal coordinate system is determined and compared with the safety distance. If the distance between the projections of the spheres along anyone of the axes exceeds the safety distance then the real distance between the spheres also must exceed the safety distance and no further calculation will be necessary.

An apparatus comprising an arrangement for carrying out the method is characterized in that the arrangement comprises a storing device for storing the coordinates for the centrum points of a number of virtual spheres, which together approximate the outer contour of the part and the further bodies, and the size of the radius of each sphere, a calculating unit for repeatedly calculating during a motion, by means of the said centrum point coordinates and the position indications of the transducers, the prevailing position of the centrum points of the spheres and for calculating thereafter, by means of these obtained centrum positions and the known radii of the spheres, the distance between those spheres which represent the moving part and those spheres which represent the further body, and comparison means for comparing each calculated distance with a safety distance.

Suitably the transducers can be of such a construction that each transducer delivers a signal representing the absolute deviation of the body in a given motion direction relative to a zero or reference position in this direction, in which case according to another feature for the invention the values stored in the storing device represent the centrum positions of the different spheres in the zero position of the respective body, while the calculating unit for each new calculation procedure makes a complete calculation of the positions of the centrum points by means of these stored values and the output signals of the transducers. By always starting in this manner from the coordinates in the zero position of the bodies and to make a complete position determination with from these values no accumulated errors will arise at the position determination.

In an anti-collision equipment it is advantageous to use two different safety distances at the comparison, in which case, if the calculated distance is below the largest safety distance, a signal appears on a first output of the calculating unit and, if the calculated distance is below the smallest safety distance, a signal will appear on a second output. These outputs then can be connected to control circuits for those motors, which cause motion in the different motion directions, which control circuits are so adapted that, when signal appears on the first output, the speed of the motors is reduced, while when signal appears on the second output, the motors are stopped.

BRIEF DESCRIPTION OF THE DRAWINGS

The invention is illustrated on the accompanying drawings, in which.

DESCRIPTION OF THE PREFERRED EMBODIMENT

Figure 1:
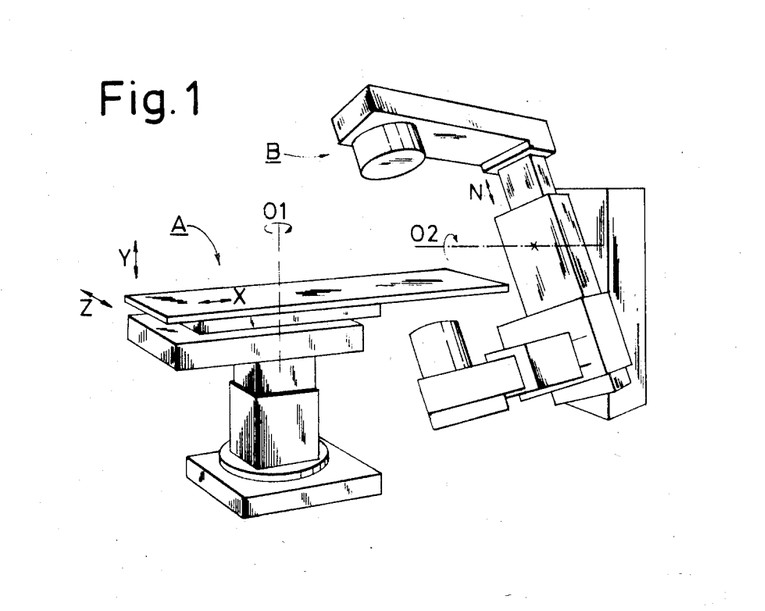
FIG. 1 shows a simplified perspective view of a medical X-ray equipment, in which the principles of the invention can be applied.

The X-ray equipment shown in FIG. 1 comprises a patient table A and an X-ray source wtih carrier B. The patient table A is linearly movable in the directions X, Y and Z and rotatable about the axis 01, while the X-ray source with the carrier B is linearly movable in the direction N and rotatable about the axis 02. Each motion is detected by means of a separate transducer, which in the present example is assumed to be of absolute value type or a so-called position transducer. Each transducer delivers a magnitude which represents the position of the respective body relative to a zero or reference position in the actual motion direction. As an example a rotary potentiometer can be mentioned, which is directly connected to the respective body and delivers a voltage representing the position of the body in the actual direction. The same type of transducer or any other suitable type of transducer is arranged for each motion direction. Thus in each moment of a motion thus transducer magnitudes are available, which unambiguously define the position of the respective body in space relative to a fixed zero or reference position.

In the following description only the two bodies A and B will be regarded but it is to be understood that all parts, which move in another manner than A and B, must be treated per se in the same manner as will be described for the bodies A and B.

According to the invention the output signals from the transducers are utilized together with the known shape of the respective body A and B in order to automatically determine the risk of collision and thereby to prevent collision. The method is as follows, reference being made to the FIGS. 2 and 3.

Figure 2:
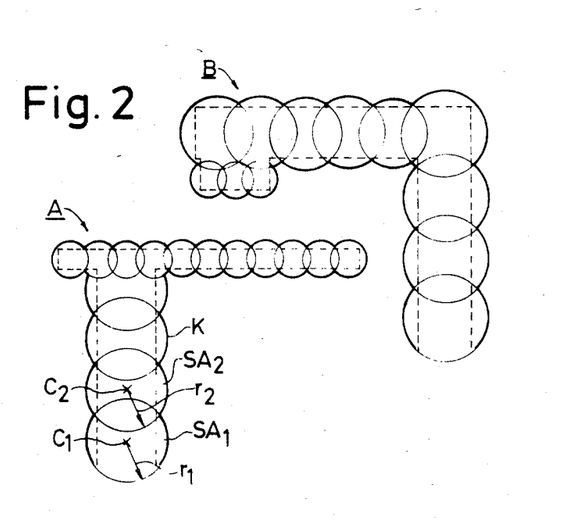
FIG. 2 shows an example on how the outer contour of components in the equipment according to FIG. 1 can be represented by a number of spheres.

Each body A, B, ... is drawn in all three projections with the bodies in their zero or reference position, as is illustrated for one projection in FIG. 2, where the contour of the respective body is shown by means of a dashed line. The outer contour is then approximated by means of a number of spheres, $SA_1$, $SA_2$, ... the size and position of which being selected such that the resulting contour, shown by means of a heavy line K, will run immediately beyond the real contour. The larger the number of spheres is, the better the approximation will be, but the larger the data quantity will also be, which must be stored and processed. Thereafter a coordinate system is selected, as is illustrated by means of the coordinate system, x, y, z in FIG. 3, and the coordinates for the centrum points $c_1$, $c_2$, ... of each sphere in the selected coordinate system are determined and stored together with the size of the radius $r_1$, $r_2$, ... of each sphere.

Figure 3:
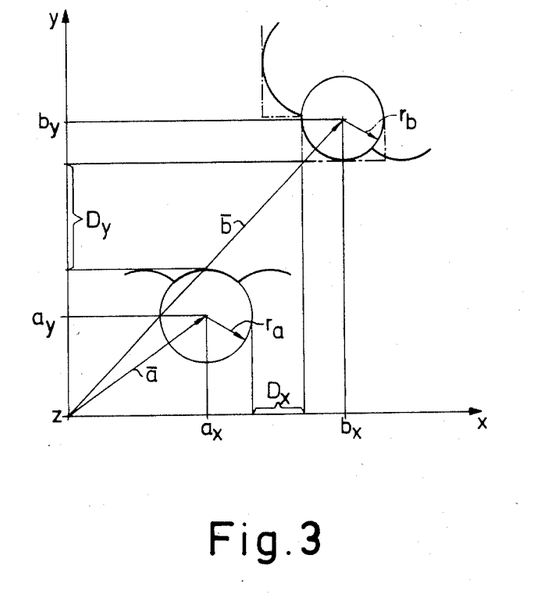
FIG. 3 shows two of the spheres in FIG. 2 in an enlarged scale and a coordinate system for enabling a mathematical definition of the positions of the spheres.

In FIG. 3 the x- and y-coordinates for the centrum point of a regarded sphere on the body A are designated with $a_x$ and $a_y$, while the corresponding coordinates for a sphere on the body B are designated with $b_x$ and $b_y$. Thus, it is these values $a_x$ and $a_y$, $b_x$ and $b_y$ and the non-visible coordinate values $a_z$, $b_z$ which are stored together with the associated radii $r_a$ and $r_b$ for all spheres. This is a basic information which is fixed and which is retrieved and used at each calculation. Suitably it may be stored in a ROM.

The basic principle for the determination of the collision risk is then that the stored coordinate values by means of the transducer signals are transformed to those coordinate values, which represent the actual position of the centrum point of each sphere, whereafter the distance between each sphere on one body and each sphere on the second body is calculated. The following is then valid (see FIG. 3):

Each centrum point can be defined by a vector a and b, respectively, which can be written:

$$\bar{a} = a_x \bar{e}_x + a_y \bar{e}_y + a_z \bar{e}_z \qquad (1)$$

$$\bar{b} = b_x \bar{e}_x + b_y \bar{e}_y + b_z \bar{e}_z$$

where $\bar{e}_x$, $\bar{e}_y$ and $\bar{e}_z$ are unit vectors along the respective axis x, y and z.

The above expression (1) is valid if the bodies A and B are in the zero position. If this is not the case the vectors will have other positions and other coordinate values along the different axes. The vectors now can be written:

$$\bar{a}' = a_x' \bar{e}_x + a_y' \bar{e}_y + a_z' \bar{e}_z \qquad (2)$$

$$\bar{b}' = b_x' \bar{e}_x + b_y' \bar{e}_y + b_z' \bar{e}_z$$

In case of a combined motion each submotion is regarded separately. Then the following is valid for the body A:

$$F_x(\bar{a}) = (a_x + \Delta x)\bar{e}_x + a_y \bar{e}_y + a_z \bar{e}_z \qquad (3)$$

$$F_y(\bar{a}) = a_x \bar{e}_x + (a_y + \Delta y)\bar{e}_y + a_z \bar{e}_z$$

$$F_z(\bar{a}) = a_x\bar{e}_x + a_y\bar{e}_y + (a_z + \Delta z)\bar{e}_z$$

$$R_x(\bar{a}) = a_x\bar{e}_x + (a_y\cos\theta_x + a_z\sin\theta_x)\bar{e}_y - (a_y\sin\theta_x - a_z\cos\theta_x)\bar{e}_z$$

$$R_y(\bar{a}) = (a_x\cos\theta_y - a_z\sin\theta_y)\bar{e}_x + a_y\bar{e}_y + (a_x\sin\theta_y + a_z\cos\theta_y)\bar{e}_z$$

$$R_z(\bar{a}) = (a_x\cos\theta_z - a_y\sin\theta_z)\bar{e}_x - (a_x\sin\theta_z - a_y\cos\theta_z)\bar{e}_y + a_z\bar{e}_z$$

where $F_x(\bar{a})$, $F_y(\bar{a})$ and $F_z(\bar{a})$ is the new vector after linear displacement a distance $\Delta x$ along the x-axis, a distance $\Delta y$ along the y-axis and a distance $\Delta z$ along the z-axis, respectively, and $R_x(\bar{a})$, $R_y(\bar{a})$ and $R_z(\bar{a})$ is the new vector after rotation an angle $\theta_x$ about the x-axis, $\theta_y$ about the y-axis and $\theta_z$ about the z-axis, respectively. The magnitudes $\Delta x$, $\Delta y$, $\Delta z$, $\theta_x$, $\theta_y$ and $\theta_z$ are received directly from the transducers cooperating with the body A.

The new coordinate values $a_x'$, $a_y'$ and $a_z'$ in the relationship (2) are determined by the relationship (3).

For the body B the new coordinate values $b_x'$ $b_y'$ and $b_z'$ are determined in the same manner as $a_x'$, $a_y'$ and $a_z'$ for the body A.

For the distance D between the centrum points of the two spheres then the following relationship is valid:

$$D = \sqrt{(a_x' - b_x')^2 + (a_y' - b_y')^2 + (a_z' - b_z')^2} \quad (4)$$

and for the distance L between the spheres the following relationship:

$$L = D - (r_a + r_b) \quad (5)$$

It is this distance L, which indicates the risk of collision and which can be compared with a safety distance, suitably two different distances.

The procedure at the calculation of the risk of collision is as follows (a complete calculation is carried out for each new sampling of the transducers):

First the position of the centrum point of each sphere is determined by means of the stored values $a_x$, $a_y$, $a_z$, $b_x$, $b_y$, $b_z$, ... and the output signals of the transducers $\Delta x$, $\Delta y$, $\Delta z$, $\theta_x$, $\theta_y$ and $\theta_z$ according to the relationship (3). Thereafter the distance L between each sphere on the body A and each sphere on the body B is calculated according to the relationships (4) and (5). Each calculated distance L is compared with a safety distance $S_1$ and if $$L > S_1 \quad (6)$$

then no measures are taken and the calculated value on L is thrown away.

In the contrary if $$L < S_1 \quad (7)$$

then this is an indication about risk of collision and results in the present example in an automatic braking of the motions of the bodies, so that these bodies thereafter will move with reduced speed.

Thereafter the calculated distance is compared with a second safety distance $S_2$ which is smaller than $S_1$. If $$L > S_2 \quad (8)$$

then no measures are taken and the bodies can continue to move. In the contrary if $$L < S_2 \quad (9)$$

then stop signal is delivered to all motors and the motion of the bodies A and B is stopped at the same time as the condition "STOP" is indicated. The stop condition will persist until a push button with the text "OVERRIDE" is actuated, which means that the described supervision system is put out of function. The bodies are thereafter free to move without supervision of possible risk of collision. This disconnection of the automatic system can be used in order to be able to escape from a stop and blocking condition but also in certain investigations for being able to bring the bodies A and B closer to each other than is possible with the used safety distance.

As it is only of interest to know if the distance between the bodies is larger than the safety distance or not but not to know how large the distance is, a simplified calculating model can be used in order to reduce the calculating work. According to this simplified model the real distance between the spheres is not calculated according to the relations (4) and (5), instead only the distance between the projections of the spheres on the x-axis, y-axis or the z-axis is determined and compared with the safety distance. If the bodies are situated in the zero-position it is consequently the distances $D_x$ and $D_y$ shown in FIG. 3 which are compared with the safety distance. If any of these distances is larger than the safety distance then also the real distance must be larger then the safety distance and the calculating process for these two spheres can be terminated. This simplified calculating model corresponds to that the outer contour of the bodies is approximated with cubes instead of spheres, as indicated in FIG. 3 by the dashed and dotted lines. The coarser approximation this involves (the error $< r_a + r_b$) is in most cases sufficient, whereby the calculating work is reduced essentially. Transition from this simplified model to calculation of the real distance according to the relationships (4) and (5) involving transition from cubic to spherical representation of the outer contour of the bodies is not made until the obtained distances are below the safety distance in all three projections.

Figure 4:
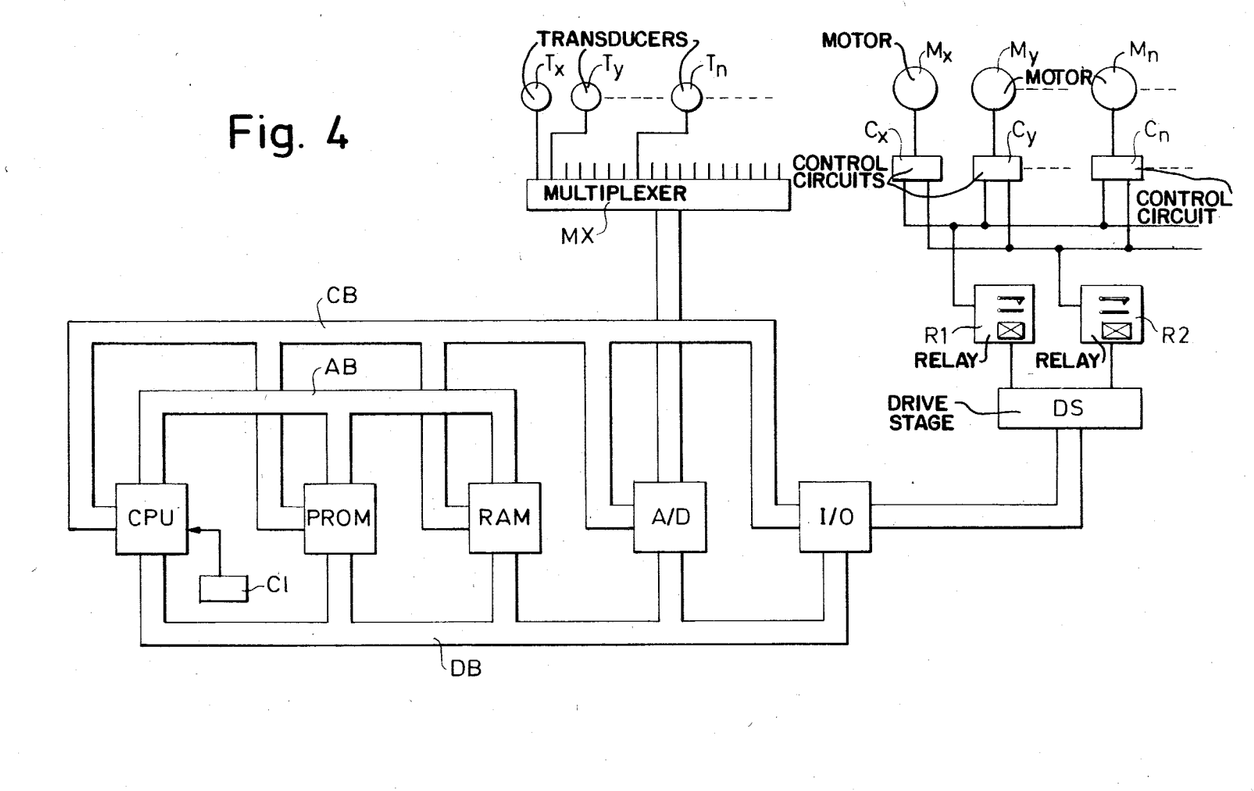
FIG. 4 shows a simplified block diagram for an arrangement according to the invention comprising a microprocessor.

FIG. 4 is a block diagram showing the hardware build-up of an anti-collision system operating in accordance with the principles of the invention and comprising a microcomputer. This computer contains a central processing unit or microprocessor designated CPU in the FIG. 4 and is in a realized embodiment implemented as a circuit type Z-80 from ZILOG. Except this component the block CPU contains circuits for bus handling and generation. The central processing unit CPU is controlled by a block C1 which in the example operates at a frequency of 2.5 MHz. Furthermore the computer comprises two memories PROM and RAM. The PROM has in the realized embodiment a capacity of 12 kBytes and is composed by 6 circuits of type 2716 Eprom. Except these 6 circuits the block PROM in FIG. 4 contains circuits for bus handling. The RAM has a capacity of 8 kBytes and is composed by 16 circuits of type 2114, static RAM, plus circuits for bus handling. The CPU, the PROM and RAM are mutually interconnected via an address bus AB, a control bus CB and a data bus DB. The control bus and the data bus also lead to an analog-to-digital converter A/D and an input output unit I/O. The unit A/D is in the given example a 12 bit converter of type AD 574 from Analog Devices, while the unit I/O is a ZILOG circuit of type Z-80 PIO. The A/D converter is connected to a multiplexer MX which in the example has 16 analog inputs. Connected to these inputs are transducers $T_x$, $T_y$ ... $T_n$ ..., which are sensitive for the position of the bodies in the respective motion direction. The unit I/O is connected to a drive stage DS for two relays R1 and R2, the contacts of which being connected to different inputs on control circuits $C_x$, $C_y$ ... $C_n$ ... associated to drive motors $M_x$, $M_y$ ... $M_n$ ... These motors produce the motion in the respective motion direction. The drive stage DS is so constructed that, when a given first signal is obtained from I/O, the first relay $R_1$ is excited, while, when a given second signal is obtained from I/O, the second relay R2 is excited. The control circuits for the motors are then so adapted that, when the first relay is actuated, all motors are brought to operate with reduced speed and, when the second relay is actuated, all motors are stopped.

Before being used the equipment is programmed so that the basic information in the shape of the co-ordinate values for the centrum points of the selected spheres, when the bodies are in the zero or reference position, are stored in the memory PROM together with the size of the radii of the spheres. In the PROM are also introduced all instructions which are necessary for calculating the distance between the spheres of one body and the spheres on a second body and comparing this distance with two different safety distances.

When the equipment then operates in its normal operation mode the CPU fetches its instructions from the PROM by addressing the PROM via the address bus and control the transmission via the control bus. The information is then exchanged via the data bus. Access to the RAM is made in the same manner via the address bus and this memory RAM is used for storing different values used during the calculation procedure. In each program loop also the A/D-converter is controlled via the control bus, so that the analog input signals are stored in the RAM via the data bus. Due to the presence of the multiplexer the different analog values can be fetched in successive order. If the calculation results in that all calculated distances are larger than the largest safety distance then no activation of the I/O takes place and the same calculation procedure is carried out for new values from $T_x$, $T_y$ ... $T_n$ ... If the comparison between a calculated distance and the safety distances shows that the calculated distance is smaller than the largest safety distance but larger than the smallest safety distance then the unit I/O is actuated via the control bus so that it delivers an actuation signal for the relay R1. This relay functions and the motors are brought to operate at reduced speed. If the comparison shows that the calculated distance also is smaller than the smallest safety distance then the I/O unit is actuated to deliver an actuation signal for the relay R2. This relay functions and the motors are stopped.

Figure 5:
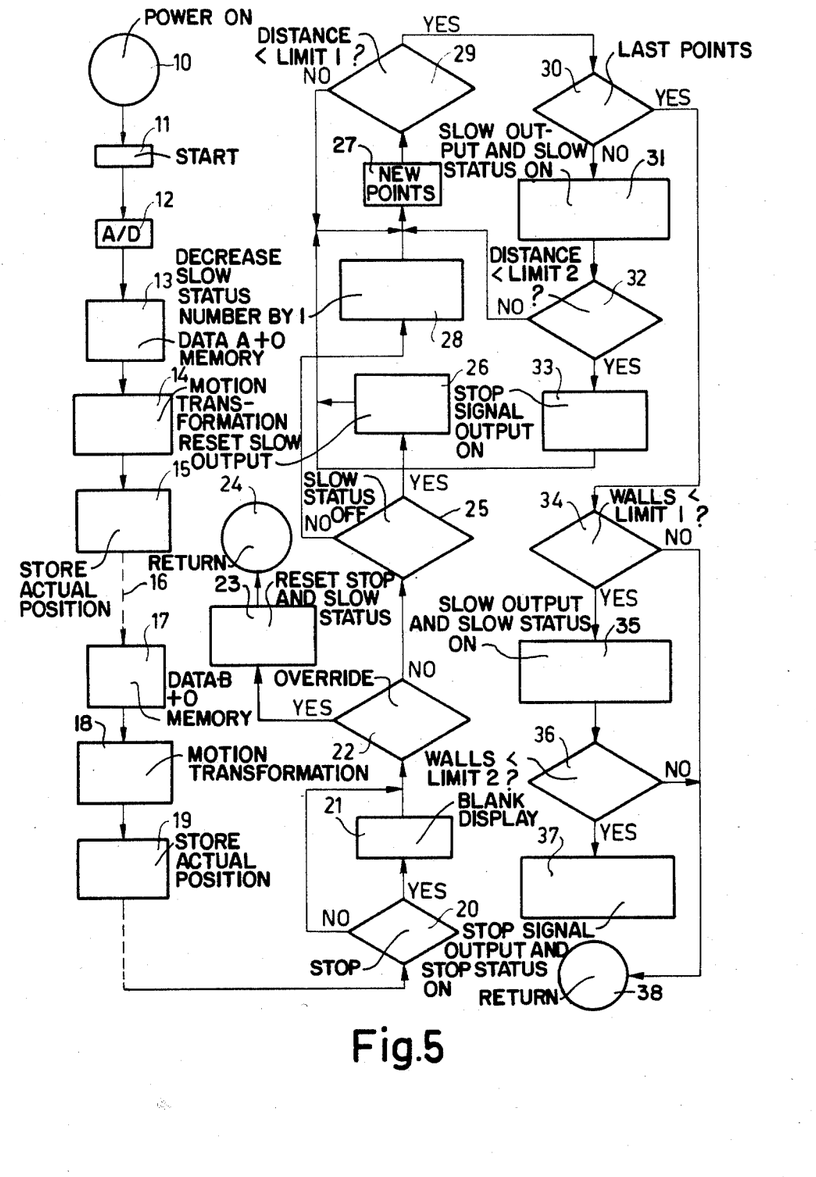
FIG. 5 shows a flow diagram for illustrating the operation in an arrangement according to FIG. 4

FIG. 5 shows a flow diagram which can be basic for a programming of the microprocessor.

The program starts at 10 "POWER ON" where driving voltage is fed to the device followed by the block 11 "START" involving normal start routines. Thereafter follows the block 12 designated "A/D" where the output signals of the transducers are digitized and stored in a buffer memory. Thereafter follows the block 13 with the text "DATA A TO MEMORY". Here the zero-coordinate values $a_x$, $a_y$, $a_z$ and the radii $r_a$ for all spheres on the body A are loaded into the working memory. In the block 14 with the text "MOTION TRANSFORMATION" then these coordinate values by means of the stored values of the output signals of the transducers are transformed to the prevailing coordinate values according to the relationship (3). The obtained results are then stored which is represented by the block 15 with the text "STORE ACTUAL POSITION". The positions of the centrum points of all spheres on the body A are now stored. The same thing is then repeated for all parts which are mechanically connected to the body A but move in another manner than A, which is represented by the dashed line 16.

In the block 17 all data for the body B are transferred in the same manner to the working memory, in the block 18 the stored information is transformed to the actual position and in the block 19 the obtained results are stored, which is then repeated for all parts connected to the body B. Now the working memory contains information about the actual position of all spheres and their size.

The program has now arrived to square 20 with the text "STOP?". Here it is investigated if a stop condition has occurred during a preceding calculating procedure, i.e. if the calculated distance has come below the smallest safety distance. This is effected by investigating the condition of a memory cell which is used for indicating such event. If the answer is "YES" the program proceeds to the block 21 "BLANK DISPLAY" and therefrom to square 22. An indicator lamp then receives extinguishing impulse and will deliver a twinkling light due to rapid repetition of the described procedure (the start routine lights the lamp each program cycle). If the answer is "NO" the program proceeds directly to square 22. In the square 22 with the text "OVERRIDE?" it is investigated if the automatic anti-collision supervision system is disenabled or not, which is effected by investigating the condition of a manually actuatable switch, which is used for effecting such disenabling. If the answer is "YES" then the program proceeds to block 23 with the text "RESET STOP AND SLOW STATUS" and thereafter to 24 representing a return routine. The block 23 involves that memory cells used for indicating a stop condition or the condition reduced speed are reset. Is the answer "NO" then the program proceeds to square 25 with the text "SLOW STATUS OFF?". Slow status means that the calculated distance was below the largest safety distance during a foregoing calculating procedure. The first time it happens this is indicated so that a digit 1 is written into certain stages of a 8-bit binary counter representing a number $\tau \leq 255$. The number $\tau$ is for example $\approx 25$ corresponding to a time delay of 5 seconds. As long as a digit 1 is written into any of the stages of the binary counter this indicates the condition "SLOW STATUS" and the motors are brought to run with reduced speed. The square 25 thus involves an investigation if the said binary counter is in the condition "0". Is the answer "YES" then the program proceeds to block 26 with the text "RESET SLOW OUTPUT", which means that the output ($OUT_1$ in FIG. 4) effecting the slow motion is inactivated. Thereafter comes the block 27 "NEW POINTS" involving that new centrum points on the bodies A and B are retrieved for distance comparison. Is the answer in the square 25 "NO", which thus involves that the condition "SLOW STATUS" prevails, then the program proceeds to a block 28 with the text "DECREASE SLOW STATUS NUMBER WITH 1" involving that the number written into the said counter is decreased with one. When the condition "SLOW STATUS" has been reached it is consequently not possible to escape from this condition until $\tau$ operation cycles of the described calculation procedure have been carried through. The intention with this is that it hereby will be possible to return to rapid motion only with an appreciable delay, while transition to the slow motion takes place immediately when the calculated distance comes below the safety distance. From 28 the program proceeds to the block 27 which involves that new centrum points for distance determination are catched. The distance determination is effected in square 29 with the text "DISTANCE<LIMIT 1?". Here it is investigated if the distance between the two regarded spheres is smaller than the largest safety distance $S_1$. The signal processing represented by the square 29 can either involve a complete distance determination according to the relationship (4) and comparison according to the relationship (5) or the previously mentioned simplified calculating model, which will be further described in connection with FIG. 6. Is the answer in square 29 "NO" then the program returns to 27 and the comparison is repeated for new centrum points and thus new spheres. Is the answer in square 29 "YES" then the program proceeds to square 30 with the text "LAST POINTS?". It is observed that, if the simplified calculating model is used, then the program is automatically switched to the exact calculation according to the relationships (4) and (5) before the answer "YES" is delivered in square 29.

It is furthermore ensured that the answer "YES" is generated at the very last points, which are tested in square 29. For proper functioning of the program imaginary points are added to the available real points which generates a "YES" response in block 29 for leaving the loop 29–27 after testing all real points. In square 30 it is investigated if the compared points are the last ones to be compared according to the adopted comparison sequence or not. Is the answer "NO" then the program proceeds to the block 31 with the text "SLOW OUTPUT AND SLOW STATUS ON". This means that the said output, which effects reduced speed of the motors, is activated and that said 8-stages binary counter indicating the condition "SLOW STATUS" is set in the position $\tau$. From 31 the program proceeds to square 32 with the text "DISTANCE<LIMIT 2". Here it is investigated if the distance between the two regarded spheres calculated in square 29 is smaller than the smallest safety distance or not. Is the answer "NO" then the signal processing is terminated for these two spheres and the program returns to block 27, where the centrum points for two new spheres are catched. Is the answer "YES" then the stop signal output is activated, which is represented by the block 33 "STOP SIGNAL OUTPUT ON". Hereby all motors are stopped. Thereafter the program returns to 27 and new points are retrieved.

Is the answer in square 30 "YES" involving that the treated points are the last ones to be processed then the program proceeds to square 34 with the text "WALLS<LIMIT1?". Here it is investigated if the distance between the spheres representing the outer contour of the movable bodies A and B and the fixed walls is smaller than the largest safety distance $S_1$. Is the answer "NO" then the signal processing for the regarded sphere is terminated represented by a return routine 38. Is the answer "YES" then the output, which effects the slow motion, is activated and the number $\tau$ is written into the said 8-stage binary counter, which is represented by the block 35 "SLOW OUTPUT AND SLOW STATUS ON", whereafter the program proceeds to square 36 with the text "WALLS<LIMIT 2?". Here it is investigated if the said distance to the fixed walls is smaller than the smallest safety distance. Is the answer "NO" then the signal processing is terminated. Is the answer "YES" then the output, which effects the stopping of the motors, is activated together with a memory cell indicating the stop condition, which is represented by the block 37 "STOP SIGNAL OUTPUT AND STOP STATUS ON".

Figure 6:
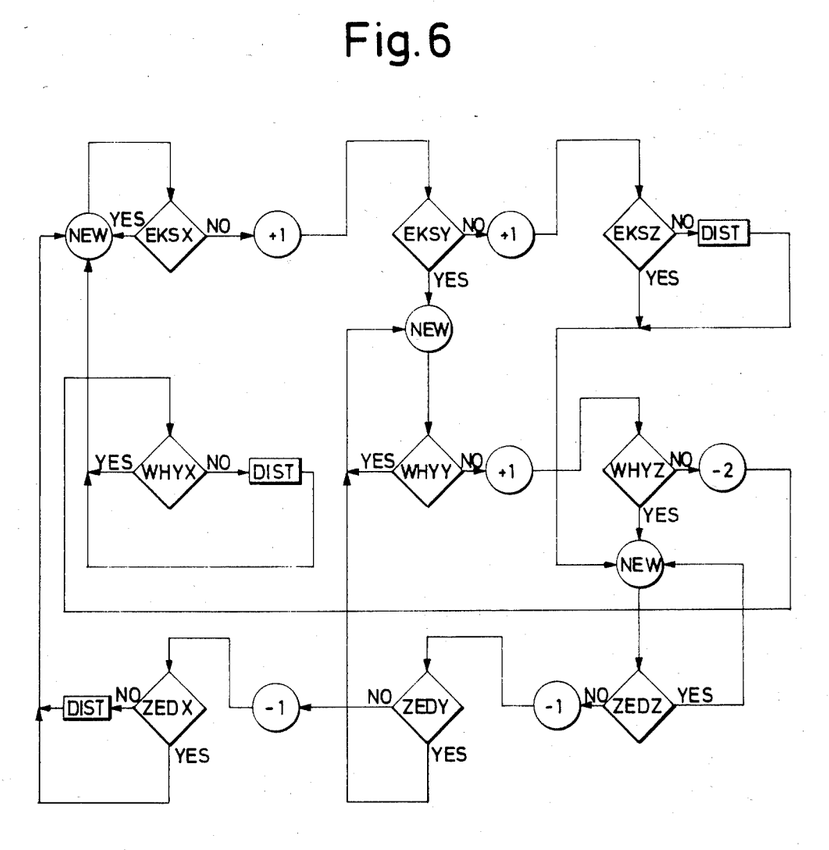
FIG. 6 shows a flow diagram relating to a subroutine in the flow diagram according to FIG. 5.

FIG. 6 shows a flow chart for said simplified calculating model involving that the spheres in this stage are approximated with cubes. The program consists of three identically equal chains each comprising three processing stages: The first chain comprises the stages called EKSX, EKSY and EKSZ followed by a stage called DIST, the second chain comprises the stages WHYY, WHYZ and WHYX followed by the stage DIST and the third chain comprises the stages ZEDZ, ZEDY and ZEDX followed by the stage DIST. Assume that the program always starts in the square EKSX. Here the question is asked: Is the distance between the projection of the two regarded spheres on the x-axis larger than the largest safety distance? If the answer is "YES" then no further signal processing regarding the two actual points (spheres) is carried through and two new points are retrieved represented by the stage NEW. The same thing is repeated for these points and if the answer is still "YES" then new points are retrieved etc. As long as the calculated distances along the x-axis are larger than the largest safety distance thus no other signal processing takes place than that represented by the square EKSX. But as soon as the answer to the question in the square EKSX is "NO" the condition of an address pointer is increased with one, represented by the circle "+1" involving that the program proceeds to square EKSY. Here the question is asked: Is the distance between the projections of the two regarded spheres on the y-axis larger than the largest safety distance? Is the answer "YES" then no further signal processing for these two points takes place and two new points are retrieved represented by the circle NEW, whereafter the program proceeds to square WHYY. Here the same question is asked regarding these new points, i.e. "is the distance between the projection of the two regarded spheres on the y-axis larger than the largest safety distance?". As long as the answer is "YES" always new points are retrieved and the same question is made for these. Thus, the distance determination now has been transferred to the y-axis. Should the answer in square EKSY be "NO" then the address pointer is increased with one represented by the circle "+1" involving that the program proceeds to EKSZ. Here the question is asked "is the distance between the projections of the two regarded spheres on the z-axis larger than the largest safety distance?". Is the answer "YES" than the signal processing for these two points is terminated and two new points are retrieved represented by the circle NEW, whereafter the program proceeds to the square ZEDZ. Here the same question is asked and as long as the answer is "YES" always new points are retrieved. The comparison now has switched over to the z-axis.

Should the answer in square EKSZ be "NO" involving that the two regarded spheres resulted in the answer "NO" in the squares EKSX, EKSY and EKSZ in succession, i.e. that the distance between the spheres along all axes is smaller than the largest safety distance, then the program proceeds to the block DIST. Here the real distance between the two actual spheres is calculated according to the relationship (4), whereafter this distance is compared with the safety distance. The result of this comparison is then used to initiate the procedures, which have been described previously in connection with the description of the main program.

If the distance determination has switched over to the y-axis via square WHYY and the answer in this square is "NO" then the address pointer is increased with one represented by the circle "+1" so that the distance determination is transferred to the z-axis represented by the square WHYZ. Is the answer in this square also "NO" then the address pointer is decreased with two, so that the distance determination switches over to the x-axis represented by the square WHYX. Should the answer again be "NO" thus involving that the two regarded spheres resulted in smaller distance than the safety distance along all axes but this time with start along the y-axis, then along the z-axis and finally along the x-axis, then the program proceeds to the block DIST, where again the exact distance between the spheres is determined and compared with the safety distance and new points are retrieved. The same thing is repeated when starting along the z-axis, represented by the square ZEDZ, in which case the program in case of the answer "NO" proceeds to ZEDY and if the answer is still "NO" to ZEDX and therefrom to the block DIST. The three blocks designated "DIST" thus represent one and the same calculation program, namely determination of the distance in accordance with the relationship (4). In this manner the required calculation work is minimized because, in most cases, measurement along one axis is sufficient.

What is claimed is:

1. An improved method to determine the risk of collision for two mutually movable bodies, whose movements are sensed by transducers for continuous monitoring of the position of the bodies during a motion, said method including the steps of:

determining repeatedly the position for the centrum of a number of virtual spherical subvolumes, whose outer circumferences together approximate the outer contour of each body during the motion; and calculating the distance between the outer circumferences of those subvolumes which represent the outer contour of one of the bodies and the outer circumferences of those subvolumes which represent the outer contour of a second body by determining the centrum positions and the known diameters of the subvolumes; and comparing each calculated distance with a safety distance; wherein the improvement comprises representing the spheres by cubes in the first calculation step thereby taking into account only the projections of the spheres on the axes in an orthogonal coordinate system at the distance determination between the spheres.

2. An improved apparatus having at least one motor-driven element and including a circuit for preventing collision of said element and a body, said motor-driven element being provided with transducers for sensing the momentary positions of said motor-driven element during a motion, said apparatus also including:

storing device for storing the coordinates of the centrum points of a number of virtual spheres, whose outer circumferences approximate the outer contour of the element and a body, and the value of the radius of each sphere;

a calculating unit for repeatedly calculating during the motion, by means of the said centrum point coordinates and the position indication of the transducers, the current position of the centrum points of the spheres and for calculating thereafter, by means of these centrum positions and the known radii of the spheres, the distance between those spheres which represent the element and those spheres which represent the body; and comparison means for comparing each calculated distance with a safety distance;

each transducer delivering a signal representing the absolute deviation of the element in a given motion direction relative to a zero or reference position in this direction;

the values stored in the storing device representing the centrum positions of the different spheres, when the bodies are situated in the said zero or reference position; and means in said calculating unit, at each calculation process, to carry out a complete position determination of the centrum positions of the different spheres by means of these fixed stored values and the output signals of the transducers; wherein the improvement comprises:

means in the calculating unit to determine the distance between the projections of a first pair of spheres on the axes in an orthogonal coordinate system and, as long as the distance between the projections of each of these spheres on the actual axis exceeds a given value, to terminate the signal processing for the first pair of spheres and to start distance determination along the same axis for a second pair of spheres.

3. An apparatus as claimed in claim 2, wherein, if the distance between the projection of the first pair spheres along one axis is below a given value, the calculation unit has means to initiate determination of the distance between the projection of the spheres along another axis and, when the distance between the projection of the spheres along all three axes is below the given value, to calculate the real distance between the spheres for comparing this distance with the safety distance.

4. An apparatus as claimed in any one of claims 2 or 3, wherein the comparison means include means to compare the calculated distances with two different safety distances, and that signal appears on a first output, when the calculated distance is below the larger safety distance, while signal appears on a second output when the calculated distance is below the smaller safety distance.

5. An apparatus as claimed in claim 4, wherein said outputs are connected to control circuits for the motors, which cause motion in the respective motion direction, which control circuits are so constructed that, when signal appears on the first output, the speed of the motors is reduced and that, when signal appears on the second output, the motors are stopped.

* * * * *